US006966345B2

(12) United States Patent  
Lönneborg et al.

(10) Patent No.: US 6,966,345 B2  
(45) Date of Patent: Nov. 22, 2005

(54) METHOD FOR DURABILITY TREATMENT OF A PUMPABLE MATERIAL AS WELL AS A DEVICE THEREFOR

(75) Inventors: Nils-Gunnar Lönneborg, Västerås (SE); Jan Hjelmqwist, Västerås (SE); Ulf Odebo, Västerås (SE)

(73) Assignee: Flow Holdings GmbH (SAGL) Limited Liability Company, Mezzovico (CH)

( * ) Notice: Subject to any disclaimer, the term of this patent is extended or adjusted under 35 U.S.C. 154(b) by 274 days.

(21) Appl. No.: 10/429,226

(22) Filed: May 1, 2003

(65) Prior Publication Data

US 2004/0118868 A1 Jun. 24, 2004

Related U.S. Application Data

(60) Provisional application No. 60/380,328, filed on May 13, 2002.

(30) Foreign Application Priority Data

May 6, 2002 (SE) .................................... 0201357

(51) Int. Cl.[7] ............................................... B65B 1/20
(52) U.S. Cl. ............................. 141/11; 141/69; 141/89
(58) Field of Search ............................ 141/1, 2, 11, 12, 141/69, 70, 82, 85, 89, 95; 100/269.01, 269.14; 222/394, 402.2

(56) References Cited

U.S. PATENT DOCUMENTS 4,501,383 A 2/1985 Iannelli ........................ 222/82

2004/0074404 A1 * 4/2004 Hellgren .................. 100/269.01

FOREIGN PATENT DOCUMENTS

| DE | 32 02 455 A1 | 10/1986 |
| DE | 35 10 859 A1 | 10/1986 |
| DE | 196 43 669 A1 | 4/1998 |
| EP | 0 891 714 A2 | 1/1999 |
| FR | 2 442 018 | 7/1980 |
| WO | WO 94/20406 | 9/1994 |
| WO | WO 96/35632 | 11/1996 |
| WO | WO 97/37892 | 10/1997 |
| WO | WO 99/47432 | 9/1999 |

* cited by examiner

Primary Examiner—Timothy L. Maust  
(74) Attorney, Agent, or Firm—Seed Intellectual Property Law Group PLLC

(57) ABSTRACT

A method for durability treatment or sterilization of a pumpable material by high pressure treatment of the same in a high pressure press for killing and/or inactivating harmful microorganisms and enzymes in the material includes placing the pumpable material into a flexible bulk container with a larger volume than the end-user or consumer containers in which the material is intended to be packed, placing the bulk container in a high pressure press and subjected to high pressure treatment, removing the bulk container from the press. The material may be moved from the bulk container to end-user containers by arranging, in a sterile manner provided, connector on the bulk container, which, via a tube connects the interior of the bulk container with an emptying system, for the purpose of draining the pumpable material into the end-user or consumer containers, or into an intermediate storage tank.

4 Claims, 5 Drawing Sheets

Figure 1:
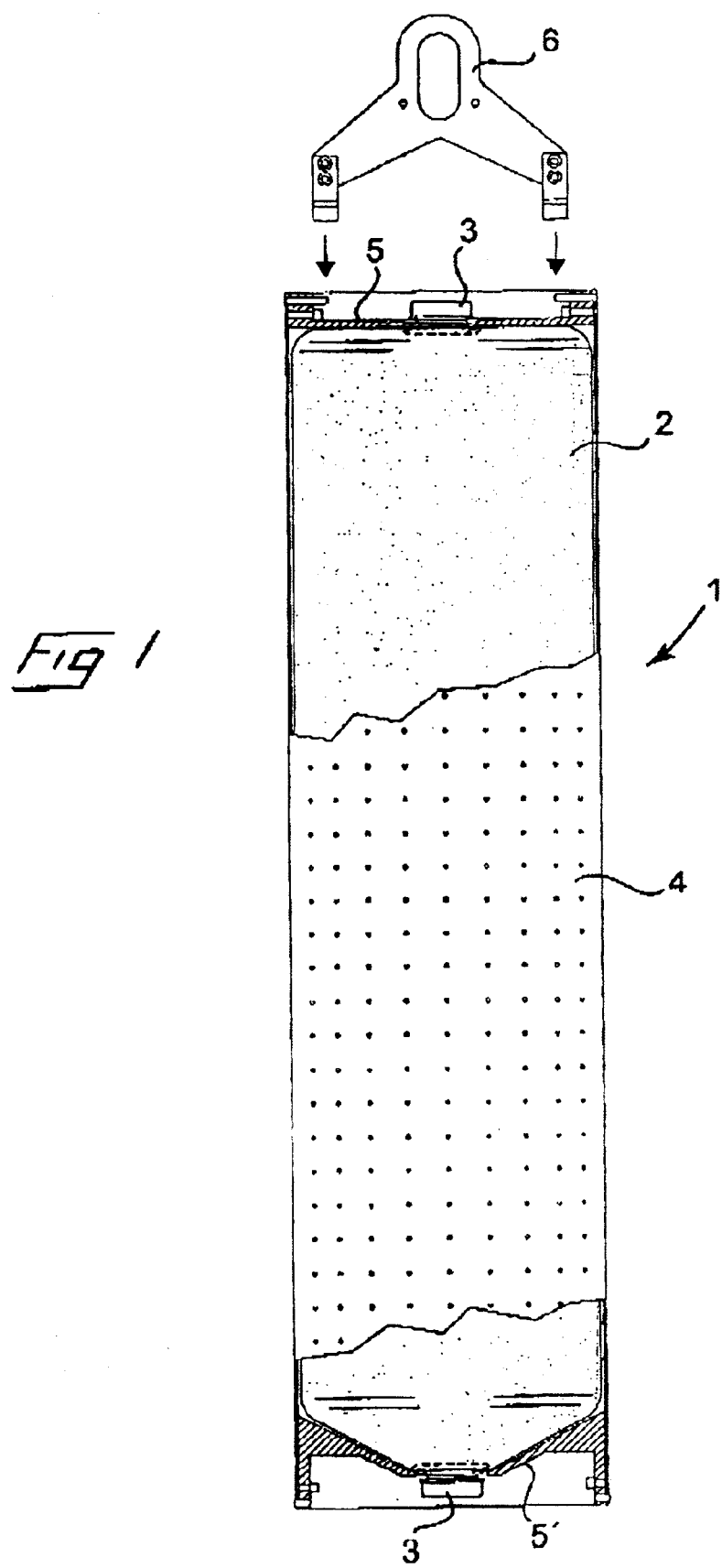

METHOD FOR DURABILITY TREATMENT OF A PUMPABLE MATERIAL AS WELL AS A DEVICE THEREFOR

The present invention relates to a method and a device for durability treatment or sterilisation of a pumpable material by high pressure treatment of the same in a high pressure press for rendering harmful microorganisms and enzymes in the material harmless and/or inactivating them.

BACKGROUND ART

Especially in the food, cosmetics and drug industry, but also in other fields, there is a need to be able to perform in a rational manner durability treatment or sterilisation of a pumpable material, such as a liquid or suspension, in larger batches than the end-user or consumer containers which are intended to hold the material, without risking contamination of the material with pollutants, such as microorganisms, during, and particularly after, the actual process of filling the end-user or consumer containers. In connection with activities with stringent cleanliness requirements, all objects and surfaces that have contacted non-cleaned air are considered contaminated. Via these objects and surfaces, pollutants may enter the pumpable material in connection with treatment and emptying and have a detrimental effect on its durability, taste, smell and the like.

Such durability treatment in large batches occurs by pasteurisation, i.e. heating of the material, in large tanks or the like. However, such a method involves drawbacks owing to the fact that much energy must be supplied in pasteurisation in order to heat the entire volume, and the process is time-consuming on the one hand because of the time it takes to heat the entire volume and, on the other hand, because the heat treatment must proceed for a certain length of time for all microorganisms safely to be rendered harmless. For instance, the outer parts of the liquid volume may be subjected to extremely long heat treatment for the central parts to obtain an acceptable heat treatment time. Many pumpable materials, especially foodstuffs, are sensitive to high temperatures and long heat treatments and may be negatively affected, with regard to consistency as well as smell and taste, during such treatments.

Durability treatment of pumpable materials is also known to take place by radioactive irradiation. In the case of irradiation of large batches, the problem arises that radiation efficiency decreases with the length of the distance that the radiation must cover in the pumpable material. There is thus a risk that the radiation dose in the centre of the liquid volume will be too small to achieve a sufficient durability treating effect. Alternatively, such high radiation doses must be applied that other negative consequences arise, such as problems of the working environment.

The most common method in heat treatment and irradiation is to carry out the treatment in a continuous flow in a portion of a pipe. In the heat treatment, the pumpable material is caused to flow past heat exchangers and be heated by them whereas in irradiation the pumpable material flows through an irradiated area in the pipe. In such a method, the drawbacks in connection with treatment of large batches at a time are eliminated, viz. that the outer portions of the volume will be excessively treated while the central portions tend to be insufficiently treated. However, there remains the problem that heat treatment requires much energy and certain materials can be negatively affected while irradiation may involve problems of the working environment. However, also the problem remains that the pumpable material must be treated in a sterile manner in the continued handling, such as filling end-user containers, which must normally be carried out in immediate connection with the durability treatment owing to the difficulties in intermediate storing and transporting the pumpable material before filling the end-user containers.

DE 3 510 859 discloses durability treatment or sterilisation of a pumpable material, which however is not described in more detail, and subsequently filling the material into bulk containers, so-called bag-in-box bulk containers consisting of a plastic bag enclosed in a cardboard box or the like. When the bulk container is to be filled or emptied, this must take place in a sterile manner. For this reason, a tapping device is connected to a sealed tapping flange on the bulk container in such a manner that the tapping device, in a first step, is arranged round the tapping flange, and then the space between the tapping flange and the tapping device is sterilised by steam. Finally, a cap nut of the tapping device is screwed onto an outer thread of the tapping flange so that a pointed hose connecting piece of the tapping device penetrates a pharmaceutical injection plug or a sealing washer in the tapping flange. Before filling the pumpable material into the bulk container, the container must be carefully cleaned by means of a cleaning agent or sterilised by, for instance, irradiation. Such a method enables intermediate storing and/or transporting of the pumpable material before filling it into end-user containers. The method involves, however, a complicated and time-consuming procedure of sterile filling of the durability treated pumpable material into the bulk container as well as sterile emptying of the same. Moreover the bulk container must be sterilised separately before filling, for instance by irradiation, which results in an additional time-consuming step of handling.

Durability treatment in the form of high pressure treatment in large batches has also been tested. Then the pumpable material is filled directly into the high pressure press so as to be in contact with the boundary walls of the press chamber. This requires, however, cleaning of the press between different shifts and also between high pressure treatments of different types of pumpable materials. The difficulty in cleaning the press therefore often results in potential colonies of bacteria of the pumpable material remaining in corners, bends and the like. In this case there is also a risk that a pressure medium, such as water or oil, leaks into the press chamber and is mixed with the pumpable material.

The normal process in durability treatment by high pressure has therefore been to subject the pumpable material to high pressure treatment in the end-user containers. In the high pressure treatment, the material is subjected to a pressure of at least 2000 bar and preferably 6000–7000 bar, at which pressure certain microorganisms and enzymes are killed or inactivated. This is possible only on the condition that the container is suited for such high pressure treatment, which requires, inter alia, the container to be flexible in at least one direction since the volume of a liquid or suspension is compressed by about 15% in high pressure treatment to this pressure. Moreover, there should be no gas in the container since this would cause compression to increase drastically. The drawback of such a process is that end-user containers are usually relatively small and high pressure treatment thereof one by one will not be rational. Certainly it is in many cases possible to stack a large number of end-user containers in a high pressure press and subject them to high pressure treatment in one and the same step, but depending on the shape of the end-user containers, the volume of the high pressure press will usually be poorly utilised, and besides a further, time-consuming operation will be added, viz. stacking the end-user containers in the manner that is most optimal for pressing. The process also limits the type of end-user containers that may be used since not all are suited for high pressure treatment, such as glass bottles and other hard containers.

In addition to the above drawbacks, there are a number of advantages of high pressure treatment compared with other methods of durability treatment. For instance, the high pressure treatment results in a durability treatment which is kind to the pumpable material, in comparison with heat treatment, so-called pasteurisation, which must be carried out at such a high temperature and for such a long time that the qualities of the product, such as smell, taste and consistency, risk being deteriorated. In heat treatment of large batches of a pumpable material, the outer portions of the volume may also be damaged owing to excessive action of heat for too long a period while the central portions will be insufficiently treated owing to insufficient action of heat for too short a period and therefore risk obtaining too short a shelf life. The drawback of high pressure treatment is that up till now it could not be performed in a simple, rational and hygienic manner.

DETAILED ACCOUNT OF THE INVENTION

The present invention aims at improving prior-art technique for durability treatment of pumpable materials and providing a method for durability treatment, which enables efficient, kind and cost-saving durability treatment. At least this object is achieved by a method according to claim 1.

Thus, the invention is based on the knowledge that the above objects can be achieved by filling the pumpable material that is to be subjected to durability treatment into a flexible bulk container, i.e. a bulk container which is considerably larger than the end-user or consumer containers in which the product is intended to be finally stored, by high pressure treating the bulk container at a pressure of at least 2000 bar, preferably at least 4000 bar and most preferably at least 6000 bar, and then, either immediately or after a certain time of intermediate storage, carrying out sterile emptying for the purpose of emptying and packing the pumpable material in the end-user or consumer containers in which the material is to be kept before use.

This method provides a number of advantages compared with prior-art methods for durability treatment. By keeping the pumpable material in a flexible bulk container during the durability treatment, it is possible to use in a rational manner the high pressure treatment which is advantageous in relation to other durability treatments with respect to e.g. care, rapidity and consumption of energy. In high pressure treatment, an instantaneous effect is achieved by increasing the pressure in the entire volume at the same time, i.e. all parts of the liquid column are subjected to the same treatment, which makes it possible to optimise the durability treatment in a manner which is completely different from other methods of durability treatment. The active effect of the high pressure treatment is besides obtained by interaction between pressure increase and a moderate adiabatic temperature increase in the entire volume at the same time, both having an inhibiting or destructive effect on the microorganisms that are present in the material. Moreover high pressure treatment has a significantly lower energy consumption than heat treatment. In the high pressure treatment, it is possible to use the capacity of the press optimally by adjusting the shape and size of the bulk container to the size and shape of the press chamber. Since the bulk container is kept in the press during the high pressure treatment, no separate careful cleaning or sterilisation of the bulk container is necessary since this is achieved simultaneously with the durability treatment of the pumpable material. Nor does the connecting means need to be connected in a sterile manner during filling, but the pumpable material can without stringent cleanliness requirements be filled into the bulk container just before the high pressure treatment. After the high pressure treatment, the bulk container is removed from the press and can be stored in this state for a period which is dependent on the intensity of the high pressure treatment, i.e. at what pressure and for how long the high pressure treatment was carried out. As a rule, it is for economic reasons desirable to perform high pressure treatment with an intensity that is not higher than absolutely necessary. In the case when the high pressure treatment is so intensive that complete sterilisation of the pumpable material is obtained, a bulk container can usually be kept in intermediate storage for one or more years in the unopened state. On the other hand, in a more normal durability treatment, the period of intermediate storage may amount to perhaps one or a few weeks.

The possibility of intermediate storage of the high pressure treated bulk containers can be used for buffering between the high pressure treatment and the subsequent packing process. This means that the capacity of high pressure press can be utilised maximally even if the packing system must be stopped for service or repair, and vice versa, if the high pressure press must undergo service or repair, the packing process can proceed as long as the buffer stock lasts. High pressure treatment in bulk containers also allows that the pumpable material can be easily produced and subjected to durability treatment in one location and then transported to another location for filling into end-user containers. Besides, optional types of end-user containers can be used.

High pressure treatment in bulk containers according to the invention also requires that the pumpable material can be emptied, in a rational and, from the viewpoint of cleanliness, reliable manner, from the bulk container to be filled into end-user containers. Therefore the invention also relates to a method and a device for emptying a pumpable material from a closed bulk container according to claims 4 and 5, respectively, and more specifically, the invention aims at a method of enabling simple and preferably automatic emptying of a pumpable material from a bulk container without risking contamination of the material with pollutants.

The above objects are achieved by a method which involves arranging at least one socket- or cup-like connecting means, which has an open end defined by an abutment edge, adjacent to, but without contact with, one of the boundary walls of the bulk container and, in this position, supplying a sterilising agent to the connecting means and the abutment area between the connecting means and the bulk container. The sterilising agent can be of an arbitrary type, for instance hot steam which, with the abutment edge of the connecting means arranged at a distance of one or a few millimetres from the wall of the bulk container, is allowed to flow into the inner space of the connecting means, towards the open end and out through the gap between the abutment edge and the wall of the bulk container. If this passage of steam is allowed to proceed for a sufficiently long period, all surfaces in the interior of the connecting means as well as the abutment edge and the abutment area of the bulk container will be sterilised. The sterilising agent, however, can be some other arbitrary, sterilising gas or liquid.

After sterilisation, the connecting means is arranged in a tight-fitting manner on the wall of the bulk container.

Subsequently a penetration tube located in the connecting means and sterilised during the sterilising moment is pressed through the wall of the bulk container. By this, the material in the bulk container can be emptied through the penetration tube without any risk of contamination since all surfaces in or round the connecting area have become sterilised.

If the bulk container is compressible, it may be sufficient to make a single connection of the type described above since the bulk container can be compressed during emptying. In many cases it is preferred, however, to make two such connections, preferably one in the top of the bulk container and one in its bottom, which means that the material is pumped out through the lower connecting means while sterilised gas, for instance nitrogen gas, flows in through the upper. To accelerate emptying, the gas can also be injected at a pressure above atmospheric so as to expel the pumpable material.

The connecting means can be arranged on any surface of the bulk container. Since the penetration tube makes a hole in the wall of the bulk container, this will imply, however, that this part of the bulk container can only be used once and then must be rejected or mended. According to a preferred embodiment of the invention, the bulk container is therefore formed with at least one, but preferably two holes or openings which are sealable with a cap, preferably a screw cap. It is possible to arrange the connecting means on a cap and let the penetration tube penetrate therethrough. In this way, the bulk container can be reused and only the caps need be replaced before each new filling and emptying cycle.

A device according to the invention comprises a socket- or cup-like connecting means which has an open end defined by a circumferential abutment edge. To allow the connecting means to be arranged in a tight-fitting manner on the wall of the bulk container, the cup of the connecting means must be tight with tight connections for operating and feeding pipes. For the same reason, it is usually also advantageous if the abutment edge is positioned in a single, common plane so as to allow a flat and tight abutment against the wall of the bulk container.

Inside the connecting means there is a penetration tube, which has a point directed towards the open end of the connecting means and which is movable between a retracted position and an extended position.

The penetration tube has an inner bore whose cross-sectional dimension is adapted for transporting the pumpable material or alternatively also sterilising gas/liquid and/or expulsion gas.

Pressing of the connecting means against the bulk container to establish tight abutment can be carried out in different ways, for instance by simply pressing the connecting means against the bulk container by means of hydraulic or pneumatic pistons. In the preferred embodiment, however, the bulk container has the form of a flexible bag of plastic which is accommodated in a pipe of perforated sheet metal. As a result, the bulk container will be quite resilient and it may be difficult to achieve tight and safe abutment between the connecting means and the wall of the bulk container, i.e. the actual bag or the cap, by pressing, merely from outside, the connecting means against the bulk container. To obviate this problem, the bulk container is therefore at its lower and upper end provided with an externally threaded opening socket onto which the sealing cap is threaded. In the preferred embodiment, the connecting means is in turn formed with gripping arms which can grip the edges of the cap and press the abutment edge against the outside of the cap.

The above-mentioned DE 3 510 859 discloses a device for carrying out sterile emptying from a bulk container. This device comprises a cup-like connecting means which is sealingly connected round an opening socket of the bulk container. Subsequently, the space between the connecting means and the opening socket is sterilised by a sterilising agent, preferably steam. For this to take place, the connecting means must be provided, not only with inlets, but also with outlets to allow steam to flow into the space between the connecting means and the opening socket and then out from this space. Such outlets cause an increased risk of microorganisms entering the space after completed sterilisation and during the emptying procedure. To have the connecting means abutting close to the bulk container during sterilisation also means that the abutment surfaces between the connecting means and the bulk container will not be sterilised and there is thus a risk that pockets with harmful microorganisms may remain and possibly be transferred to the pumpable material during emptying. Having connected the connecting means to the opening socket and having performed the sterilisation, a cap nut is to be screwed, manually or by means of a tool, onto an outer thread of the opening socket. The cap nut in turn causes a penetrating means to penetrate a cap over the opening socket. A great drawback of the such a device is that it is difficult to automate and requires more or less manual handling during emptying.

In an embodiment, the bulk container has the form of a bag of plastic with a volume of about 200 l, which is held in a perforated sheet metal pipe. The pipe is provided with an upper and a lower end piece with recesses for the opening sockets. However, it should be understood that the bulk container can be designed in many other ways and in other sizes and, in an alternative embodiment of the invention, a bulk container made of a thicker plastic is shown and described, which does not need an outer pipe to be supported. An important feature, however, is that the bulk container is flexible in one direction for it to be deformed in connection with the decrease in volume of the pumpable material during the high pressure treatment. Preferably, the bulk container is also adjusted to the press space in the high pressure press so as to fill up this space as completely as possible and, thus, optimally utilise the capacity.

Preferably, the connecting means for emptying the bulk containers are arranged at a special emptying station to which the bulk containers are moved, possibly after some time of intermediate storage and/or transport, after the durability treatment. Then the pumpable material is emptied, in a sterile manner, from the bulk container and is passed, preferably through pipes, to a buffer or storage tank and then on to an aseptic container filling machine. However, it would also be possible to conduct the pumpable material directly to the container filling machine without any intermediate buffer tank. Before that, the system of pipes is sterilised with e.g. steam. After emptying, the bulk container is transported back to a filling station where it is provided with new caps and filled with a new batch. It should also be understood that the pumpable material can be emptied from the bulk container in an arbitrary, sterile manner, and not only according to the method and by means of the device as described and according to the embodiment which is illustrated in the Figures and described in the following detailed description.

BRIEF DESCRIPTION OF THE ACCOMPANYING DRAWINGS

Figure 3:
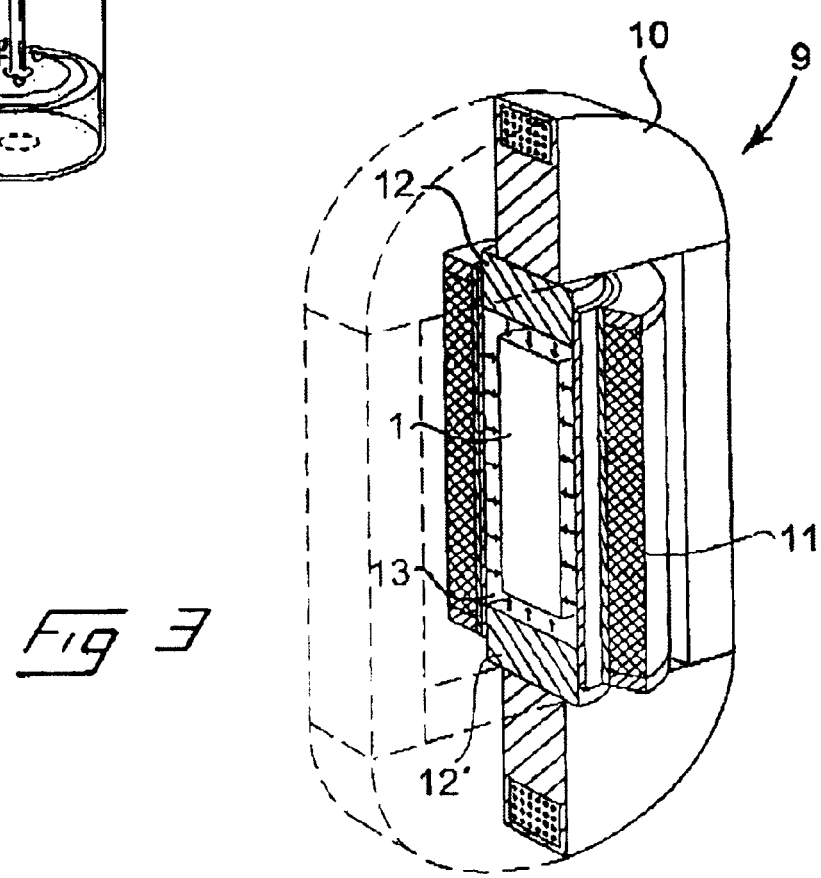
Figure 4:
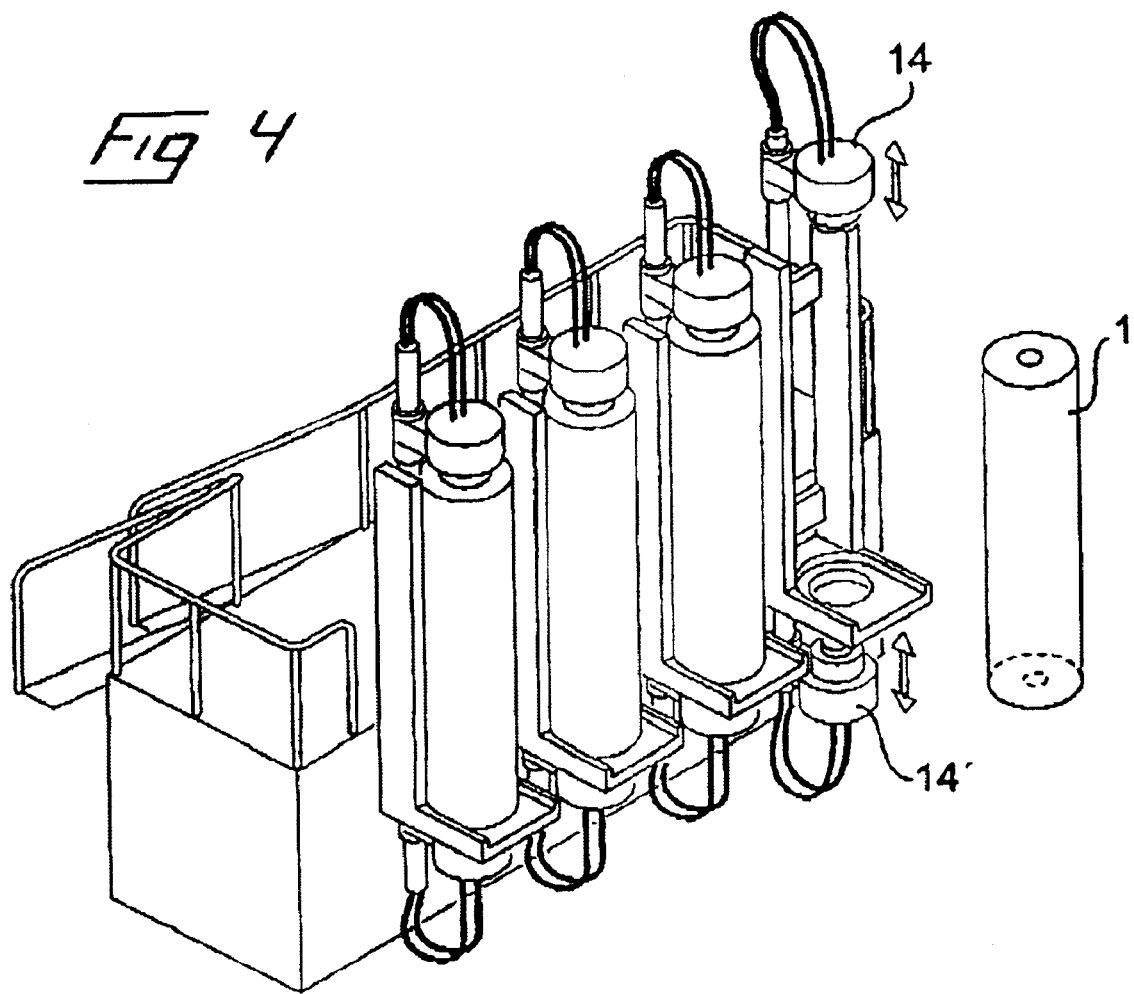
Figure 5:
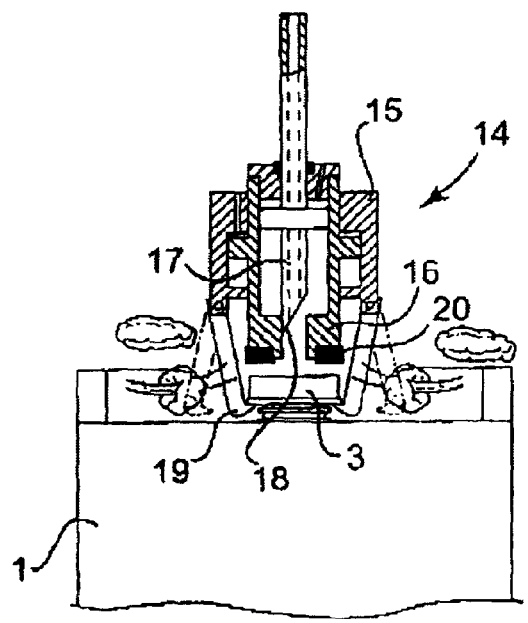
Figure 6:
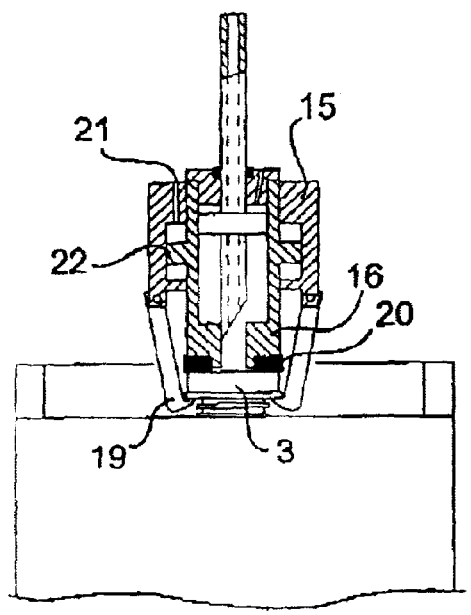
Figure 7:
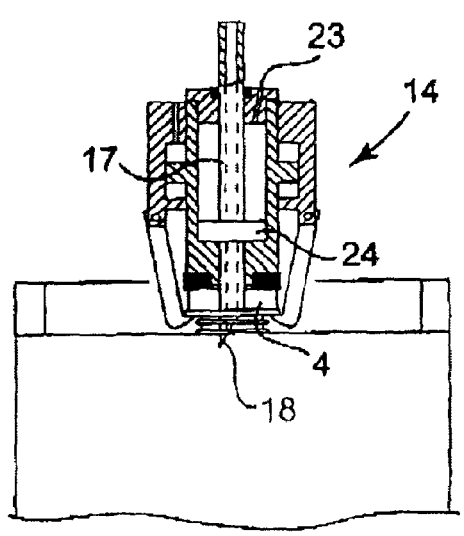
Figure 8:
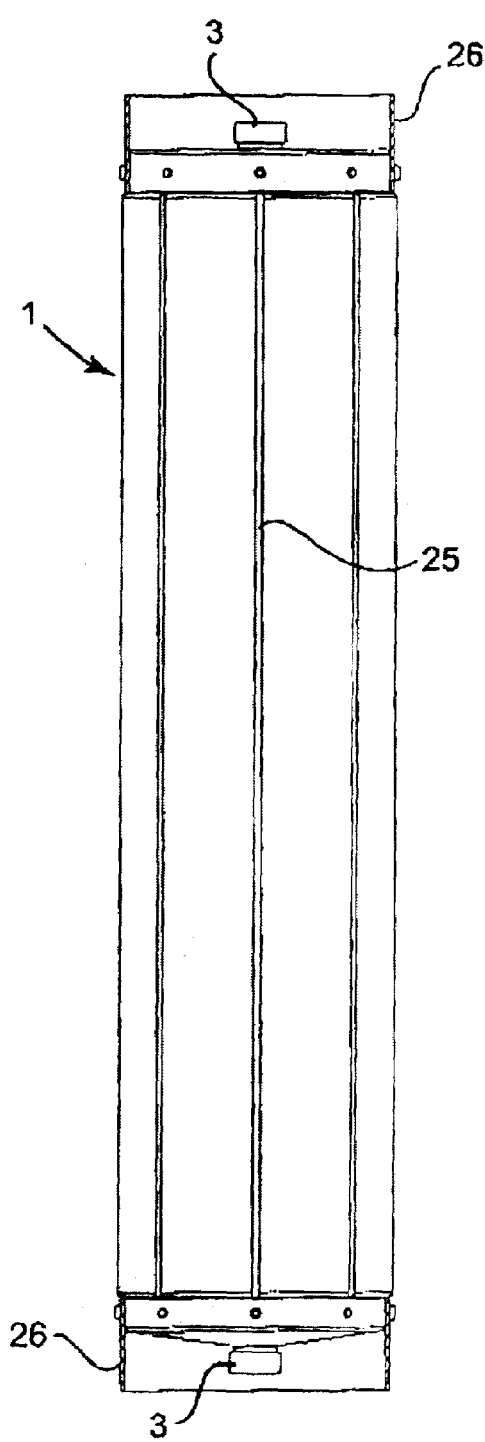
Figure 9:
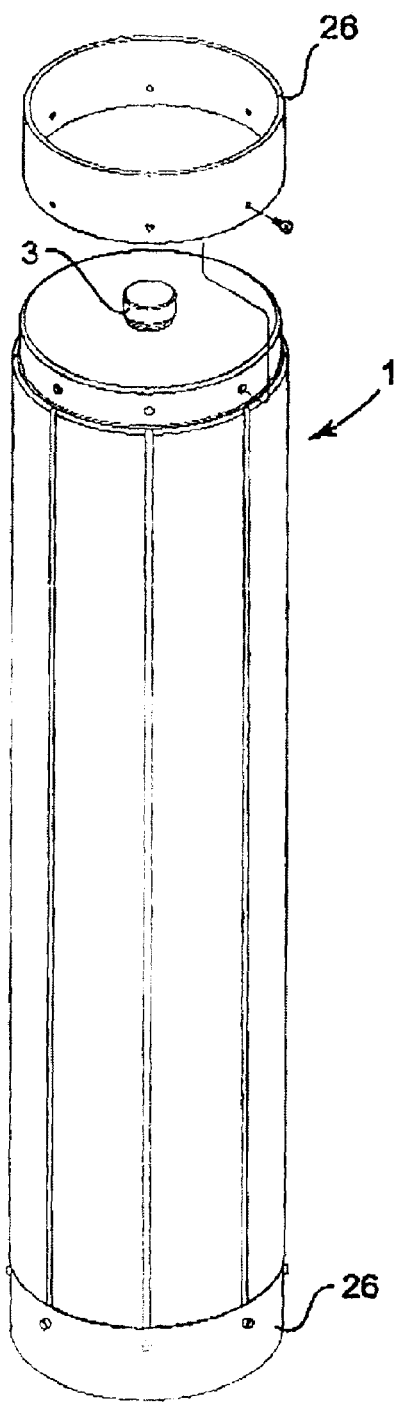

The invention will now be described with reference to the drawings which illustrate a preferred embodiment for high pressure treatment of a pumpable material and subsequent emptying of the bulk container in which the material is held. In the drawings FIG. 1 is a part-sectional side view of a first embodiment of a bulk container and a lifting yoke for handling the same, FIG. 2 is a part-sectional perspective view illustrating filling of the bulk container, FIG. 3 is a sectional perspective view of a high pressure press with a bulk container arranged in the press space and intended for a pumpable material, FIG. 4 is a perspective view of an emptying station, FIGS. 5–7 show a preferred embodiment of a connecting means for emptying the bulk container shown in three different functional steps, and FIGS. 8–9 illustrate an alternative embodiment of a bulk container shown in a side view and a perspective view, respectively.

DETAILED DESCRIPTION OF PREFERRED EMBODIMENTS OF THE INVENTION

In the following detailed description, a method for durability treatment of a pumpable material by means of high pressure treatment will be described. Reference is first made to FIG. 1 which shows an embodiment of a bulk container 1 for storing a pumpable material. The bulk container is particularly adapted for high pressure treatment and comprises an inner, thin and flexible bag 2 of plastic, preferably polyethylene. The bag 2 is at its lower and upper end provided with an opening socket with an outer thread onto which a cap 3 is screwed. The bag 2 is held in an essentially circular-cylindrical perforated sheet metal pipe 4 which at its upper and lower end is formed with an upper and lower end piece 5, 5', respectively, which each have through holes for the opening sockets of the bag. The through holes in the upper and lower end pieces 5, 5' are designed so that the opening sockets are securable to prevent both longitudinal displacement as well as turning. Owing to this design, a space is defined for the bag in the pipe 4 which limits the movement of the bag 2 but allows compression of the bag inside the pipe during the high pressure treatment while the pipe has only a carrying and supporting function for the bag during movement of the bulk container. At the upper end of the pipe, there are mountings for a lifting yoke 6 to facilitate handling of the bulk container.

Figure 2:
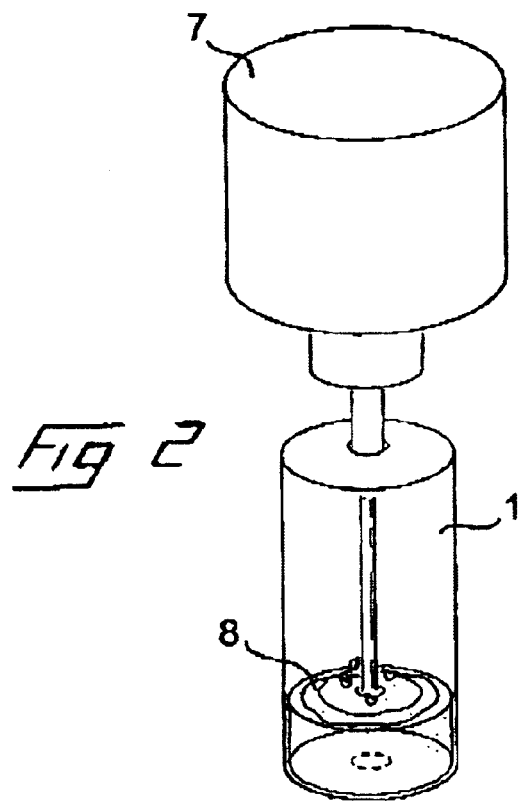

FIG. 2 illustrates schematically filling of the bulk container 1 from a storage container 7 with a pumpable material 8 which is to be subjected to durability treatment. This is carried out with the upper cap in the upper end portion of the bulk container unscrewed while the lower cap in the lower end portion of the bulk container is mounted in place and filling takes place so that as little air as possible remains in the bulk container, after which the upper cap is screwed on. Before or during this filling, no sterilisation of the pumpable material, the connecting means or the bulk container has to be made.

Subsequently the bulk container is moved to a high pressure press 9 which is schematically illustrated in a sectional perspective view in FIG. 3. However, it should be understood that this high pressure press is only an example of a high pressure press which can be used for the purpose, but that also many other types of high pressure presses can be used. The high pressure press comprises a pretensioned reinforced press frame 10, dashed lines indicating the entire outer contour of the press frame. The press frame has a central opening in which a press housing is arranged. This comprises a cylindrical column tube 11 and upper and lower end sealing elements 12, 12' which seal the ends of the column tube so that a press chamber 13 is defined therein. The press housing and the press frame can be removed from each other, in a non-pressurised state, and at least the upper end sealing element 12 is displaceably arranged in the column tube 11 and removable so that a schematically shown bulk container 1 can be placed in the press chamber 13. During pressing, water is pumped at high pressure into the press chamber through conduits (not shown) and the pressing pressure acts on the bulk container 1 from all sides. For an acceptable durability treatment of the pumpable material in the bulk container 1 by the high pressure treatment, it is usually necessary to have a pressure of between 2000 and 10000 bar for a few seconds up to about 20 min according to the type of material that is to be treated and the desirable length of storage life. At these high pressures, the volume of the pumpable material will decrease by between about 5 and 25%, which means that the volume of the bulk container, i.e. the volume of the bag 2 in a bulk container according to FIG. 1, decreases correspondingly and the temperature normally increases by between 3 and 55° C.

After the high pressure treatment, the press chamber 13 is relieved of pressure, so that the upper and lower end sealing elements 12, 12' can be displaced inwards and the press housing and the press frame can then be removed from each other to allow the bulk container 1 to be removed from the press housing. When the bulk container is to be emptied, it is moved to an emptying station as schematically illustrated in FIG. 4. At the emptying station, the bulk container 1 is placed in a stand and upper and lower connecting means 14, 14' are moved from above and from below, respectively, towards the upper and lower cap of the bulk container.

The more detailed design and function of a preferred embodiment of a connecting means according to the invention is illustrated in cross-section in FIGS. 5–7. The connecting means has an essentially socket- or cup-like shape and comprises an outer connecting means 15 and, movably arranged in the same, an inner connecting means 16. In the inner connecting means 16, a penetration tube 17 is positioned, which is in turn displaceably arranged and formed with a tip 18. Furthermore, two hook means 19 are pivotally arranged at the outer end of the outer connecting means 15.

With reference to FIGS. 5–7, the function of the inventive connecting means 14 will be described. Although the Figures only show the upper connecting means 14, it should be understood that also the lower connecting means 14' has essentially the same design and function.

FIG. 5 shows the connecting means in an initial position as it has been moved close to the cap 3 of the bulk container 1, however without being made to abut the same. The hook means 19 have in this position been pivoted inwards, with the aid of operating means (not shown), so that the hooks grip the lower edge of the cap and thus fix the connecting means and the cap in relation to each other. In this position, steam is made to flow into the inner space of the inner connecting means through the penetration tube 17 and then flow out in the inner space of the connecting means, past the tip 18 of the penetration tube 17 and through the space between the cap 3 and an outer abutment edge 20 of the inner connecting means to the surroundings. To obtain an acceptable sterilisation of all surfaces, the passage of steam should proceed for at least about 10 min.

In FIG. 6, the passage of steam has been interrupted and the inner connecting means 16 has been displaced downwards so that its abutment edge 20 and a seal located on the same abut against the outside of the cap 3. The displacement of the inner connecting means 16 is effected by applying a pressure above atmospheric, preferably pneumatically, through a duct 21 in the outer connecting means 15 to an upper pressure chamber on the upper side of a circumferential flange edge 22 of the inner connecting means. Counterforces exerted by the hook means 19 will thus firmly press the inner connecting means 16 with its abutment edge against the cap.

In FIG. 7, the penetration tube has been displaced outwards from the retracted position with the tip inside the abutment edge of the connecting means, according to FIGS. 5 and 6, to an extended position in which the penetration tube has been moved outwards with its tip 18 past the abutment edge of the connecting means and through the cap 3. The displacement of the penetration tube 17 is effected by applying a pressure above atmospheric in a duct 23 to a chamber on the upper side of a flange 24 round the penetration tube 17.

Preferably the tip 18 of the penetration tube is designed so as not to completely cut off a flap from the cap, but the flap remains fixed to the cap at an edge and is only folded away so that there is no risk of the flap getting into the pumpable material.

In the state shown in FIG. 7, a connection has been provided between the connecting means 14 at the upper end of the bulk container and 14' at the lower end of the bulk container and the inner space of the bulk container, so that the pumpable material can be emptied through the lower connecting means while gas, preferably under pressure, can flow into the bulk container through the upper connecting means.

Once the emptying is completed, the upper and lower connecting means can be removed by proceeding as described above but in reverse order, i.e. the penetration tube 17 and the inner connecting means 16 are displaced upwards while the hook means 19 are pivoted outwards. Subsequently the bulk container can be provided with new caps and filled with a new batch of the pumpable material to begin a new press cycle.

FIGS. 8 and 9 show an alternative embodiment of a bulk container 1. In contrast to the previously shown and described bulk container, this is self-supported and thus does not need any perforated sheet metal pipe to carry the liquid-tight container. Instead the bulk container is made of a thick plastic material, in the preferred embodiment about 10 mm polyethylene, which is strong enough to last also when the bulk container is completely filled with a pumpable material and which at the same time is flexible enough to withstand the deformation that arises in the high pressure treatment.

The bulk container according to FIGS. 8 and 9 is dimensioned in order to fill the press chamber as much as possible in which it is to be subjected to high pressure treatment. Since the bulk container is flexible and filled with a liquid material, it will, when placed in the press chamber, swell and completely fill the cross-section of the press chamber. To prevent the bulk container from acting as a plug that would prevent pressure medium flow from one end of the press chamber to the other and, thus, a substantially exclusively axial deformation instead of a deformation in all directions, the outer circumferential surface of the bulk container is formed with longitudinal grooves 25 which cause the pressure medium to flow from one end of the press chamber to the other and act on all outer surfaces of the bulk container.

Each end of the bulk container is provided with opening sockets which are closable by means of caps 3 of a type similar to the previous embodiment. Also filling, durability treatment and emptying are carried out correspondingly. The bulk container is also provided with a flange ring 26 at each end, serving as supports protection and attachment for lifting devices to facilitate handling.

What is claimed is:

1. A method for durability treatment or sterilisation of a pumpable material by high pressure treatment of the same in a high pressure press for killing and/or inactivating harmful microorganisms and enzymes in the material comprising:

filling the pumpable material into a flexible bulk container with a larger volume than the end-user or consumer containers in which the material is intended to be packed;

placing the bulk container in the high pressure press and subjecting it to high pressure treatment at a pressure of at least 2000 bar;

after completed high pressure treatment, removing the bulk container from the press for possible intermediate storage; and performing sterile emptying of the pumpable material from the bulk container by arranging in a sterile manner a connecting device on the bulk container, which connects the interior of the bulk container with an emptying system, for the purpose of filling the pumpable material into the end-user or consumer containers or into an intermediate storage tank.

2. The method as claimed in claim 1 wherein the bulk container is subjected to high pressure treatment at a pressure of at least 4000 bar.

3. The method as claimed in claim 1 wherein the bulk container is subjected to high pressure treatment at a pressure of at least 6000 bar.

4. The method as claimed in claim 1 wherein the sterile emptying of the bulk container comprises the steps of:

arranging a connecting device, with an open end thereof directed towards the bulk container, on a boundary surfaces of the bulk container;

supplying a sterilising agent to the connecting device for performing sterilisation of the inside thereof and a portion of the boundary surface of the bulk container;

penetrating the wall of the bulk container with a penetration tube located in the connecting device;

emptying the pumpable material in the bulk container through the penetration tube;

supplying the sterilising agent to the connecting device when it is arranged at a short distance from the boundary wall of the bulk container, so that the sterilising agent flows out between the connecting device and the boundary wall and in this way performs a sterilisation also of the abutment area between a circumferential abutment edge of the connecting device and the boundary wall; and arranging the connecting device in a tight-fitting manner on the boundary wall.

* * * * *